(12) United States Patent
Wang et al.

(10) Patent No.: US 9,028,851 B2
(45) Date of Patent: May 12, 2015

(54) HEMOSTATIC MATERIALS AND DEVICES WITH GALVANIC PARTICULATES

(75) Inventors: Yi-Lan Wang, Belle Mead, NJ (US);
Ying Sun, Belle Mead, NJ (US);
Guanghui Zhang, Belle Mead, NJ (US);
Chunlin Yang, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 375 days.

(21) Appl. No.: 13/333,136

(22) Filed: Dec. 21, 2011

(65) Prior Publication Data

US 2013/0164360 A1    Jun. 27, 2013

(51) Int. Cl.
| | | |
|---|---|---|
| *A61K 9/70* | (2006.01) | |
| *A61P 7/04* | (2006.01) | |
| *A61K 9/00* | (2006.01) | |
| *A61K 33/00* | (2006.01) | |
| *A61K 33/34* | (2006.01) | |
| *A61L 24/00* | (2006.01) | |
| *A61L 24/02* | (2006.01) | |
| *A61L 24/08* | (2006.01) | |
| *A61K 33/30* | (2006.01) | |

(52) U.S. Cl.
CPC ............. *A61L 24/0036* (2013.01); *A61K 33/34* (2013.01); *A61L 24/02* (2013.01); *A61L 24/08* (2013.01); *A61L 2400/04* (2013.01); *A61K 33/30* (2013.01)

(58) Field of Classification Search
None
See application file for complete search history.

(56) References Cited

U.S. PATENT DOCUMENTS

| | | | |
|---|---|---|---|
| 4,167,416 | A | 9/1979 | Zolla |
| 5,304,403 | A | 4/1994 | Schlesinger et al. |
| 5,589,256 | A | 12/1996 | Hansen et al. |
| 5,964,936 | A | 10/1999 | Reisser |
| 5,993,526 | A | 11/1999 | Sommer et al. |
| 6,045,570 | A | 4/2000 | Epstein et al. |
| 7,172,812 | B2 | 2/2007 | Greiwe et al. |
| 7,666,803 | B2 | 2/2010 | Shetty et al. |
| 2003/0108612 | A1 | 6/2003 | Xu et al. |
| 2005/0175649 | A1 | 8/2005 | Disalvo et al. |
| 2006/0042509 | A1 | 3/2006 | Henglein et al. |
| 2006/0084338 | A1 * | 4/2006 | Shetty et al. .................. 442/268 |
| 2006/0233869 | A1 * | 10/2006 | Looney et al. ................ 424/443 |
| 2007/0172438 | A1 | 7/2007 | Kruger et al. |
| 2008/0254147 | A1 * | 10/2008 | Huey et al. .................... 424/684 |
| 2010/0249927 | A1 | 9/2010 | Yang et al. |
| 2010/0268335 | A1 * | 10/2010 | Yang et al. ................. 623/11.11 |
| 2011/0060419 | A1 | 3/2011 | Choi et al. |
| 2011/0288026 | A1 | 11/2011 | Simpson et al. |

FOREIGN PATENT DOCUMENTS

WO    WO2011077145    *    6/2011    ............. A61F 13/36

OTHER PUBLICATIONS

Eming, S.A. et. al. 'Inflammation in Wound Repair: Molecular and Cellular Mechanisms' Journal of Investigative Dermatology (2007) vol. 127 pp. 514-525.

(Continued)

*Primary Examiner* — Mina Haghighatian
*Assistant Examiner* — Erin Hirt
(74) *Attorney, Agent, or Firm* — David R. Crichton

(57) ABSTRACT

The present invention is directed to a hemostatic material comprising a scaffold and a galvanic particulate. The galvanic particulate comprises particles made of at least two dissimilar metals. The scaffold is preferably a biocompatible polysaccharide-based hemostatic, such as a chitosan or cellulosic based hemostatic like ORC.

12 Claims, 8 Drawing Sheets

(56) References Cited

OTHER PUBLICATIONS

Sebastian, A. et. al., 'Acceleration of cutaneous healing by electrical stimulation: Degenerate electrical waveform down-regulates inflammation, up-regulates angiogenesis and advances remodeling in temporal punch biopsies in a human volunteer study' Wound Repair and Regeneration (2011) vol. 19 pp. 693-708.

Michels, H.T. et al. "*Copper Alloys for Human Infectious Disease Control*", Presented at Materials Science and Technology Conference, Sep. 25-28, 2005, Pittsburgh, PA, Copper for the $21^{st}$ Century Symposium, pp. 1-11.

Zhenguo, Zhu Ed. "Practical Physiotherapy", pp. 1-3, Published by Nanjing Publishing House, Jan. 1997.

\* cited by examiner

HEMOSTATIC MATERIALS AND DEVICES WITH GALVANIC PARTICULATES

FIELD OF THE INVENTION

The present invention relates generally to agents and devices for promoting hemostasis and, more particularly, to scaffold materials, such as oxidized regenerated cellulose based hemostatic scaffolds, having galvanic particulates that improve the hemostatic properties of the scaffold materials.

BACKGROUND

Blood is a liquid tissue that includes red cells, white cells, corpuscles, and platelets dispersed in a liquid phase. The liquid phase is plasma, which includes acids, lipids, dissolved electrolytes, and proteins. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as thrombin and fibrinogen.

Previously known TAH materials, such as gelatin, collagen, oxidized cellulose, and biologics, such as thrombin, fibrinogen, and other materials have been used, but each of these materials has limitations. Hemostatic devices containing biologics have special handling requirements in order to maintain the biologic activity. Safety is also a concern when using animal- or human-derived biologics due to contaminants or adverse immunological responses. For example, one type of prior art blood clotting materials are blood-derived proteins or enzymes, including fibrinogen and/or thrombin, which are expensive, need specialized storage conditions, and require extensive purification in order to eliminate the potential for transmission of blood-borne infections.

Published U.S. Patent Applications 2011/0060419, 2010/0268335, and 2010/0249927, all entitled "MEDICAL DEVICES WITH GALVANIC PARTICULATES", which are incorporated herein by reference in their entirety for all purposes; describe implantable medical devices having galvanic particulates. However, these references do not disclose the use of the galvanic particulates with specific hemostatic scaffolds.

Hemostatic devices containing liquid thrombin have special handling requirements in order to maintain thrombin's biologic activity. For example, liquid thrombin requires refrigeration to maintain shelf-life stability. Safety is also a concern when using animal or human derived thrombin as there are some risks of contaminants or immunogenicity. Further, thrombin and fibrinogen purified from human or animal plasma are very expensive. Therefore, it is advantageous to develop novel hemostats that can provide improved hemostatic performance, preferably materials that are not derived from animal blood origins, but have comparable performance, long shelf life and ambient conditions of storage, and low cost. There is a need in hemostatic materials with greater shelf-life stability, lower risk of viral contaminants and lower immunogenicity, low cost, and which can work in heparinized or platelet inactivated blood.

SUMMARY OF THE INVENTION

Briefly stated, the present invention is directed to hemostatic compositions, devices, and materials comprising galvanic particulates that have been combined with or incorporated into oxidized regenerated cellulose (ORC), the hemostatic materials being in either in dry format or as a wet paste. The hemostatic materials of the present invention demonstrate enhanced hemostatic performance relative to ORC and exhibit comparable or superior hemostatic efficacy relative to human thrombin mixed with gelatin based hemostatic scaffolds such as SURGIFLO® or commercially available ORC, oxidized cellulose (OC), or chitosan based products.

More particularly, the present invention is directed to a hemostatic material, comprising at least one galvanic particulate, more preferably a plurality of particulates, each particulate comprising of at least two dissimilar metals and a polysaccharide-based, biocompatible hemostatic scaffold. The galvanic particulate(s) can contain copper and zinc as the dissimilar metals. In a preferred embodiment, the plurality of particulates are dispersed within and/or on a surface of the hemostatic scaffold. The scaffold can comprise or preferably consist essentially of oxidized regenerated cellulose or chitosan. The scaffold can be in a powder or a fabric in woven or non-woven form. In one embodiment, the hemostatic device contains 0.01-10 mg of galvanic particulate per gram of the scaffold.

The present invention also relates to a method of providing a hemostatic treatment to a wound site by forming a hemostatic material comprising a scaffold, at least one galvanic particulate, more preferably a plurality of galvanic particulates, and optionally a mixing media, such as water or saline, and substantially immediately applying the hemostatic material to the wound site.

The present invention also relates to a method of making a hemostatic material by providing at least one galvanic particulate, more preferably a plurality of galvanic particulates, comprising particles made of at least two dissimilar metals and a hemostatic scaffold and distributing said galvanic particulate in said scaffold or on the surface of said scaffold.

In one embodiment, the hemostatic material and methods described above are used on a patient having platelet compromised function blood and/or heparinized blood or otherwise containing anti-clotting or anti-coagulant agents.

DETAILED DESCRIPTION OF THE INVENTION

Figure 1:
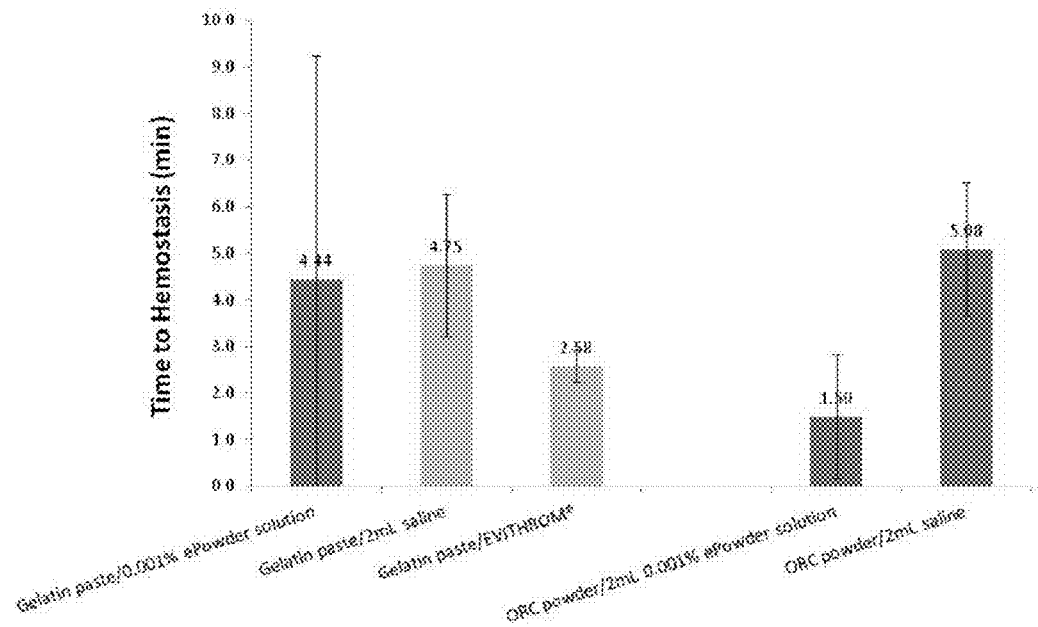
FIG. 1 shows data on time to hemostasis for several tested systems.

According to an embodiment of the present invention, the inventive hemostatic materials comprise galvanic particulates that have been combined with or incorporated into a polysaccharide-based hemostatic material, such as a cellulosic substrate, preferably oxidized regenerated cellulose (ORC)-based scaffold. The resulting hemostatic material can be in either a dry format or wet paste. The hemostatic materials of the present invention demonstrate enhanced hemostatic performance relative to ORC alone and exhibit comparable or superior hemostatic efficacy relative to human thrombin mixed with gelatin based hemostatic scaffolds, such as SURGIFLO® or commercially available ORC products. Advantageously, the hemostatic materials products are safe, and can be stored at room temperatures with no impact on hemostatic performance. Advantageously, the hemostatic materials are fully synthetic, can be produced in large quantities, and without concern of blood-borne contamination. The hemostatic material should also be biocompatible, meaning the hemostatic material should biodegrade over time into degradation products that can be eliminated naturally by a mammalian body either by secretion or incorporation into the natural biochemical cycle.

According to another embodiment of the present invention, the inventive hemostatic materials comprise galvanic particulates, that have been combined with or incorporated into a polysaccharide-based hemostatic, such as a chitosan, chitin, alginate, oxidized alginate and oxidized starch substrate, most preferably chitosan-based. The hemostatic material should also be biocompatible, meaning the hemostatic material should biodegrade over time into degradation products that can be eliminated naturally by a mammalian body either by secretion or incorporation into the natural biochemical cycle.

Further, the hemostatic materials have excellent hemostatic efficacy, are ready to use, with no preparation steps needed, can be stored at room temperature, and comparatively lower cost to produce.

According to an embodiment of the present invention, novel hemostatic materials are formed by combining galvanic particulates with a cellulosic substrate, preferably an ORC-based scaffold. The cellulosic substrate can be in a powder format or in a woven or non-woven fabric format. Additionally, binders and additives can be used to form novel hemostatic materials of the present invention.

The present invention further relates to a method of providing a hemostatic treatment to a bleeding site, comprising the steps of forming a hemostatic material as described above, and applying the hemostatic material to the bleeding site.

The present invention further relates to a method of making a dry or semi-liquid hemostatic preparation comprising the steps of mixing the cellulosic material in a powder form with galvanic particulates optionally adding water or aqueous solution such as normal saline, and immediately applying the resulting material to a wound site. The present invention further relates to a method of making a hemostatic preparation comprising the steps of applying galvanic particulates to a cellulosic-based woven or non-woven fabric, optionally adding a binder, and applying the resulting material to a wound site.

Galvanic Particulate

The galvanic particulates useful in the present invention include a first conductive material and a second conductive material, wherein both the first conductive material and the second conductive material are at least partially exposed on the surface of the particulate. In one embodiment, the particulate includes the first conductive material and the surface of the particulate is partially coated with the second conductive material. A reference is made to published U.S. Patent Applications 2011/0060419, 2010/0268335, and 2010/0249927, all entitled "MEDICAL DEVICES WITH GALVANIC PARTICULATES", which are incorporated herein by reference in their entirety for all purposes.

In one embodiment, the galvanic particulates are produced by a coating method wherein the weight percentage of the second conductive material is from about 0.001% to about 20%, by weight, of the total weight of the particulate, such as from about 0.01% to about 10%, by weight, of the total weight of the particulate. In one embodiment, the coating thickness of the second conductive material may vary from single atom up to hundreds of microns. In yet another embodiment, the surface of the galvanic particulate comprises from about 0.001 wt. % to about 99.99 wt. % such as from about 0.1 wt. % to about 99.9 wt. % percent of the second conductive material.

In one embodiment, the galvanic particulates are produced by a non-coating method (e.g., by sintering, printing or mechanical processing the first and the second conductive materials together to form the galvanic particulate) wherein the second conductive material comprises from about 0.1% to about 99.9%, by weight, of the total weight of the particulate, and other ranges for example from about 10% to about 90%, of the total weight of the particulate.

In one embodiment, the galvanic particulates are fine enough that they can be suspended in the compositions during storage. In a further embodiment, they are in flattened and/or elongated shapes. The advantages of flattened and elongated shapes of the galvanic particulates include a lower apparent density and, therefore, a better floating/suspending capability, as well as better coverage over biological tissue, leading to a wider and/or deeper range of the galvanic current passing through the biological tissue (e.g., the skin or mucosa membrane). In one embodiment, the longest dimension of the galvanic particulates is at least twice (e.g., at least five times) the shortest dimension of such particulates. In another embodiment, the shape of the galvanic particulate is a thin flake, with its thickness (Z-axis) significantly smaller than its other two dimensions (X and Y dimensions), for example, with its thickness from about 0.5 to 1.5 micrometers and its other two dimensions ranging from about 5 micrometers to about 100 micrometers.

The galvanic particulates may be of any shape, including but not limited to, spherical or non-spherical particles or elongated or flattened shapes (e.g., cylindrical, fibers or flakes). In one embodiment, the average particle size of the galvanic particulates is from about 10 nanometers to about 500 micrometers, such as from about 100 nanometers to about 100 micrometers. What is meant by the particle size is the maximum dimension in at least one direction.

Examples of combinations of first conductive materials/second conductive materials are elemental metals that include (with a "/" sign representing an oxidized but essentially non-soluble form of the metal), but are not limited to, zinc-copper, zinc-copper/copper halide, zinc-copper/copper oxide, magnesium-copper, magnesium-copper/copper halide, zinc-silver, zinc-silver/silver oxide, zinc-silver/silver halide, zinc-silver/silver chloride, zinc-silver/silver bromide, zinc-silver/silver iodide, zinc-silver/silver fluoride, zinc-gold, zinc-carbon, magnesium-gold, magnesium-silver, magnesium-silver/silver oxide, magnesium-silver/silver halide, magnesium-silver/silver chloride, magnesium-silver/silver bromide, magnesium-silver/silver iodide, magnesium-silver/silver fluoride, magnesium-carbon, aluminum-copper, aluminum-gold, aluminum-silver, aluminum-silver/silver oxide, aluminum-silver/silver halide, aluminum-silver/silver chloride, aluminum-silver/silver bromide, aluminum-silver/silver iodide, aluminum-silver/silver fluoride, aluminum-carbon, copper-silver/silver halide, copper-silver/silver chloride, copper-silver/silver bromide, copper-silver/silver iodide, copper-silver/silver fluoride, iron-copper, iron-copper/copper oxide, copper-carbon iron-copper/copper halide, iron-silver, iron-silver/silver oxide, iron-silver/silver halide, iron-silver/silver chloride, iron-silver/silver bromide, iron-silver/silver iodide, iron-silver/silver fluoride, iron-gold, iron-conductive carbon, zinc-conductive carbon, copper-conductive carbon, magnesium-conductive carbon, and aluminum-carbon.

The first conductive material or second conductive material may also be alloys, particularly the first conductive material. Non-limiting examples of the alloys include alloys of zinc, iron, aluminum, magnesium, copper and manganese as the first conductive material and alloys of silver, copper, stainless steel and gold as second conductive material.

In one embodiment, the particulate, made of the first conductive material, is partially coated with several conductive materials, such as with a second and third conductive material. In a further embodiment, the particulate comprises at least 95 percent by weight of the first conductive material, the second conductive material, and the third conductive material. In one embodiment, the first conductive material is zinc, the second conductive material is copper, and the third conductive material is silver. Standard electrode potential is potential of an electrode composed of a substance in its standard state, in equilibrium with ions in their standard states compared to a hydrogen electrode. In one embodiment, the difference of the standard electrode potentials (or simply, standard potential) of the first conductive material and the second conductive material is at least about 0.1 volts, such as at least 0.2 volts. In one embodiment, the materials that make up the galvanic couple have a standard potential difference equal to or less than about 3 volts. For example, for a galvanic couple comprised of metallic zinc and copper, the standard potential of zinc is −0.763V ($Zn/Zn^{2+}$), and the standard potential of copper is +0.337 ($Cu/Cu^{2+}$), the difference of the standard potential is therefore 1.100V for the zinc-copper galvanic couple. Similarly, for the magnesium-copper galvanic couple, standard potential of magnesium ($Mg/Mg^{2+}$) is −2.363V, and the difference of the standard potential is therefore 2.700V. Additional examples of standard potential values of some materials suitable for galvanic couples are: $Ag/Ag^+$: +0.799V, $Ag/AgCl/Cl^-$: 0.222V, and $Pt/H_2/H^+$: 0.000V. Pt may also be replaced by carbon or another conductive material. In general, the voltage between the conductive materials will be sufficient to effectively provide a desired therapeutic effect.

In one embodiment, the conductive electrodes are combined (e.g., the second conductive electrode is deposited to the first conductive electrode) by conventional chemical, electrochemical, physical or mechanical process (such as electroless deposition, electric plating, vacuum vapor deposition, arc spray, sintering, compacting, pressing, extrusion, printing, and granulation) conductive metal ink (e.g., with polymeric binders), and other known metal coating and powder processing methods commonly used in powder metallurgy, electronics and medical device manufacturing processes. In another embodiment, all of the conductive electrodes are manufactured by conventional chemical reduction processes (e.g., electroless deposition), sequentially or simultaneously, in the presence of reducing agent(s). Examples of reducing agents include phosphorous-containing reducing agents (e.g., a hypophosphite as described in U.S. Pat. Nos. 4,167,416 and 5,304,403), boron-containing reducing agents, and aldehyde- or ketone-containing reducing agents such as sodium tetrahydroborate ($NaBH_4$) (e.g., as described in published US Patent Publication No. 2005/0175649).

In one embodiment, the second conductive electrode is deposited or coated onto the first conductive electrode by physical deposition, such as spray coating, plasma coating, conductive ink coating, screen printing, dip coating, metals bonding, bombarding particulates under high pressure-high temperature, fluid bed processing, or vacuum deposition.

In one embodiment, the coating method is based on a displacement chemical reaction, namely, contacting a particulate of the first conductive material (e.g., metallic zinc particle) with a solution containing a dissolved salt of the second conductive material (e.g. copper acetate, copper lactate, copper gluconate, or silver nitrate). In a further embodiment, the method includes the step of solution flowing over the particulate of the first conductive material (e.g., zinc powder) or through the packed powder of the first conductive material. In one embodiment, the salt solution is an aqueous solution. In another embodiment, the solution contains an organic solvent, such as an alcohol, a glycol, glycerin or other commonly used solvents in pharmaceutical production to regulate the deposition rate of the second conductive material onto the surfaces of the first particulates, therefore controlling the activity of the galvanic particulates produced.

In another embodiment, the galvanic particulates of the present invention may also be coated with other materials to protect the galvanic materials from degradation during storage (e.g., oxidation degradation from oxygen and moisture), or to modulate the electrochemical reactions and to control the electric current generate when in use. The exemplary coating materials over the galvanic material(s) are inorganic or organic polymers, natural or synthetic polymers, biodegradable or bioabsorbable polymers, silica, ceramic, various metal oxides (e.g., oxide of zinc, aluminum, magnesium, or titanium) and other inorganic salts of low solubility (e.g., zinc phosphate). The coating methods are known in the art of metallic powder processing and metal pigment productions, such as those described by U.S. Pat. Nos. 5,964,936, 5,993,526, 7,172,812; Published U.S. Patent Publication Nos. 2006/0042509A1 and 2007/0172438.

In one embodiment, the galvanic particulates are stored in a dry environment. The galvanic particulates are activated by moisture to provide a galvanic battery. It is preferred that they be kept in a moisture free environment to prevent premature activation of the particles. In another embodiment, the galvanic particulates are stored in a nonconductive vehicle, such as an anhydrous solvent or a solvent mixture, which includes, but is not limited to, polyethylene glycol (PEG), glycerin, and propylene glycol.

Oxidized Regenerated Cellulose (ORC)

ORC is an absorbable hemostatic material known to these skilled the art. A number of methods are known for forming various types of hemostats based on oxidized cellulose materials into powder, woven, non-woven, knit, and other forms and combinations thereof. Currently utilized hemostatic wound dressings include knitted or non-woven fabrics comprising oxidized regenerated cellulose (ORC), which is oxidized cellulose with increased homogeneity of the cellulose fiber. Examples of such hemostatic wound dressings commercially available include Surgicel® resorbable hemostat; Surgicel Nu-Knit® resorbable hemostat; and Surgicel® Fibrillar resorbable hemostat; all available from Johnson & Johnson Wound Management Worldwide, a division of Ethicon, Inc., Somerville, N.J., a Johnson & Johnson Company.

Methods for Incorporating Galvanic Particulates into or onto Hemostatic Scaffolds According to an embodiment of the present invention, hemostatic material is formed by combining galvanic particulates from Example 1 with powdered oxidized regenerated cellulose (ORC) and aqueous media, such as normal saline, followed by a thorough mixing, to form a semi-liquid paste immediately prior to application to a wound site to arrest bleeding.

In one embodiment, the dry powders of ORC and galvanic particulates can be premixed and stored in a moisture-free environment, and then mixed with aqueous media immediately prior to application to a wound site to arrest bleeding. In another embodiment, the dry powders of ORC and galvanic particles are stored separately and then mixed with aqueous media immediately prior to application to a wound site to arrest bleeding, the mixing being performed by either simultaneously adding dry powders of ORC and galvanic particles to aqueous media or sequentially adding dry powders of ORC and galvanic particles to aqueous media in any order.

According to another embodiment of the present invention, hemostatic material is formed by combining galvanic particles with powdered Oxidized Regenerated Cellulose (ORC) followed by a thorough mixing, to form a dry powdered hemostatic material for subsequent application to a wound site in a form of dry powder to arrest bleeding.

According to yet another embodiment of the present invention, hemostatic material is formed by depositing galvanic particles on ORC based woven or non-woven fabric, optionally with addition of a binder, such as polyethylene glycol (PEG). The binder solution was prepared with PEG [mw: 3350 Daltons]/PEG [mw: 8000 Daltons]/dichloromethane (DCM), with a ratio of 1 g:1 g:100 mL (w/w/v). 100 mg of galvanic particulates was mixed with 3 mL of the binder solution. Preferably an anhydrous media, such as organic solvent or an alcohol, is used to prepare the binder solution. The galvanic particulates/binder solution was sprayed onto a pre-trimmed 3"×3" Surgicel Nu-Knit® resorbable hemostat fabric (ETHICON, Inc., Lot #3418584; Exp.: 2014-12). The galvanic particulates coated Surgicel Nu-Knit® was allowed for air dry in a laminar hood for 3 hours following by a vacuum dry for 3 days.

In one embodiment of the invention, a substantially homogenous paste is prepared by mixing the galvanic particulates and ORC powders with the liquid to form a uniform paste, which may also include effective amounts of other additives dissolved therein. Mixing may be accomplished by extrusion or by mixing in a confined space under conditions effective to provide a uniform dispersion of the solid particles in the liquid phase. Alternately, a mixer, e.g. a double planetary mixer, may be utilized in making compositions of the present invention.

Alternatively, mixing may be accomplished in multichamber syringe or utilizing two syringes interconnected by a luer and moving the mixture back and forth from one syringe to another immediate prior to application to the wound site. The liquid such as normal saline or purified water and galvanic particulates and ORC powder are added to the mixing chamber. The liquid may include effective amounts of additives dissolved therein prior to addition of particles to the solution. For example, a saline solution containing optionally glycerol and benzalkonium chloride may be prepared and then added to the mixing chamber. The solid particles or powders can be added to the mixer all at once or over time with continuous mixing until all ingredients have been added. The mixing is continued until such time as a substantially homogenous composition is formed containing the solid particles uniformly dispersed throughout the continuous liquid phase.

Hemostatic Devices

Medical devices in which the hemostatic materials and compositions of the present invention may be utilized include any device currently being used to apply a flowable or injectable hemostatic paste or slurry or powder or fabric-based hemostat to a site, or wound, requiring hemostasis.

Examples of devices or applicators include syringes such as Becton Dickinson or Monoject luer syringes. Other devices are disclosed in detail in U.S. Pat. No. 6,045,570, the contents of which are incorporated by reference in their entirety.

Sterilization

The hemostatic compositions prepared as above can be sterilized to provide sterile compositions comprising the hemostatic peptide. In some embodiments the compositions are transferred into a medical device as described above and the device containing the hemostatic composition is sterilized, preferably by ionizing radiation or by other known techniques or combinations thereof, including heat sterilization, EtO sterilization, etc. More preferably, sterilization is by gamma irradiation as exemplified herein.

Compositions of the present invention include compositions described herein that are sterile, in that they have been irradiated with a level of, e.g. ionizing irradiation. Such irradiation may include e-beam or gamma irradiation. The level of irradiation and conditions of sterilization, including the time that the compositions are irradiated, are those that provide sterile compositions, as defined herein. Once having the benefit of this disclosure, one skilled in the art will be able to readily determine the level of irradiation necessary to provide sterile compositions.

Additional Components

The hemostatic compositions may further comprise effective amounts of one or more additives or compounds including, but not limited to, antimicrobial agents, surfactants, antioxidants, humectants, wetting agents, lubricants, thickeners, diluents, irradiation stabilizers, e.g. radical scavengers, plasticizers, and stabilizers. For example, glycerol may be added to enhance the extrudability or injectability of the composition. When utilized, glycerol may be present in the compositions at from about 0% to about 20% by weight, based on the weight of the liquid phase. Preferably, the composition may comprise from about 1% to about 10% by weight of glycerol, based on the weight of the liquid phase. The compositions may comprise from about 1% to about 5% by weight of glycerol, based on the weight of the liquid phase.

In addition, quaternary amines may be used to provide enhanced properties to the compositions. For example, benzalkonium chloride, POLYBRENE™ or ONAMER M™ may be used at levels up to about 1 percent by weight, based on the weight of the liquid phase. Preferably, benzalkonium chloride is used at levels of from about 0.001% to about 0.01% by weight, based on the weight of the liquid phase. More preferably, the compositions may comprise from about 0.002 to about 0.006% by weight benzalkonium chloride, based on the weight of the liquid phase. It is believed that the quaternary amines may serve multiple functions, acting as an antimicrobial agent, a foaming agent, a radical scavenger and as a heparin neutralizer.

The hemostatic preparation can further contain effective amounts of one or more additives or compounds selected from the group consisting of antimicrobial agents, surfactants, antioxidants, humectants, wetting agents, lubricants, thickeners, diluents, irradiation stabilizers, e.g. radical scavengers, plasticizers, and stabilizers, more particularly including an extrusion enhancing amount of glycerol, and preferably wherein the glycerol is present at an amount from about 1% to about 20% by weight, based on the weight of the liquid phase of the overall hemostatic preparation.

Such hemostatic compositions may further comprise heparin neutralizers, additional procoagulants or hemostatic agents, such as thrombin, fibrinogen, fibrin, Factor Xa, or Factor VIIa. By "effective amount", it is meant that amount necessary to provide to the compositions those properties for which the additive is being added. The effective amount also is limited by the maximum amount that may be added without causing detrimental biological effects.

EXAMPLE 1

Galvanic Particulate Preparation Based on Displacement Chemistry

In Aqueous Media: 0.75% elemental copper-coated elemental zinc galvanic particulates were prepared by electroless coating of copper onto zinc powder according to the following procedure:
1) Weigh 22 g of Copper (II) Acetate into 850 ml of de-ionized water in a 1 L container, and stir until completely dissolved.
2) Weigh 930 g of elemental zinc powder (median size: 7-12 microns) into an 8 L beaker containing 2790 ml of de-ionized water. Mixing at 650 RPM or a greater speed to achieve a zinc powder suspension or slurry.
3) Under continuous mixing, add copper acetate solution from Step 1 slowly into zinc powder suspension. Continue to mix for 10 minutes
4) Charge the zinc-copper slurry into a Mini-Nutsche Filter Dryer—Bench Top (Pope Scientific Inc., Saukville, Wis., USA, equipped with 1-micron filter
5) Pressurize the Filter Dryer with air nitrogen (up to about 50 psi) to remove the water
6) Add 1 L of 100% ethanol to wash filtered galvanic particulate with agitation
7) Remove the ethanol by pressurized air nitrogen
8) Repeat the Ethanol washing process of Step 6 & 7
9) Repeat Step 6 & 7 with 2 L 100% ethanol twice
10) Dry filtered galvanic particulates with vacuum (approx. 21 Hg) for 4 hours with progressive increase of temperature up to 65° C. with periodical agitation.
11) Remove any particle aggregates of size greater than 200 microns by sieving to yield 0.75% elemental copper-coated elemental zinc Galvanic Particulate

EXAMPLE 2

Galvanic Particulates and ORC Hemostatic Paste vs. Controls

Referring now to FIG. 1, data on average time to hemostasis in minutes is presented for several tested systems, including hemostatic material containing ORC, galvanic particulates, and various controls, with typically three experiments conducted with each hemostatic material. The error bars indicate standard deviations.

On this and following charts, the designation "ePowder" is used to refer to galvanic particulates. On the chart, designation of Gelatin paste/0.001% galvanic particulates solution corresponds to a hemostatic material containing SURGIFLO® hemostatic matrix mixed with 2 mL of 0.001% galvanic particulates solution. 0.001% galvanic particulates solution is 0.001% (by weight) suspension of galvanic particulates in normal saline. One of the 3 tests with this material completely failed to achieve hemostasis.

On the chart, designation of Gelatin paste/2 mL saline corresponds to a hemostatic material containing SURGIFLO® hemostatic matrix mixed with 2 mL saline.

On the chart, designation of Gelatin paste/EVITHROM® corresponds to a hemostatic material containing SURGIFLO® hemostatic matrix mixed with 2 mL EVITHROM® thrombin solution (800~1200 IU/mL). EVITHROM® is available from Ethicon, Inc., and is containing thrombin topical (human), 800~1200 IU/mL. EVITHROM® solution containing primarily human thrombin (full composition of Evithrom® contains human thrombin (800-1200 IU/mL), calcium chloride, human albumin, mannitol, sodium acetate, and water for injection).

On the chart, designation of ORC powder/2 mL 0.001% galvanic particulates solution corresponds to a hemostatic material containing ORC powder mixed with 2 mL of 0.001% (by weight) suspension of galvanic particulates in normal saline.

On the chart, designation of ORC powder/2 mL saline corresponds to a hemostatic material containing ORC powder in the amount of 0.983 g mixed with 2 mL normal saline.

For testing article preparation, corresponding scaffold materials were thoroughly mixed with the solutions or suspensions optionally containing galvanic particulates in specified concentrations. The procedure of mixing used was as follows: 1. Draw 2 mL normal saline into an empty first syringe with a connector; 2. Pre-fill ORC powder in an empty second syringe with a corresponding connector; 3. Mix the 2 components by connecting the first and second syringes; 4. Continue to mix the components by pushing the combined material back and forth until the consistency is even, and apply to the wound.

Galvanic particulates suspensions in normal saline were prepared immediately before applied to the wound as follows. Dry galvanic particulates were pre-filled in an empty male syringe, and then were mixed with normal saline pre-filled in an empty female syringe. The paste was immediately applied to the wound by expressing the paste directly onto a wound from six (6) mL syringe in the amount of one (1 mL).

In vivo hemostatic activity study was performed using the porcine spleen biopsy punch model, with the punched wound opening six (6) mm wide×three (3) mm deep made on the spleen and the test article applied to a freshly created wound site followed by an occlusive digital pressure (tamponade). Pressure was initially applied for thirty (30) seconds and was timed using an electronic timer. Following the 30 second periods, a tamponade, digital pressure was discontinued; the gauze pad on the article was immediately removed. A 30-second hemostasis evaluation period was performed. If free flow bleeding was not observed within 30 seconds, the time to hemostasis was noted, in a minutes seconds format, and testing was concluded for that article. If free flow bleeding was observed, pressure and gauze were reapplied for additional 30 seconds tamponade and observation periods until hemostasis was achieved or until the testing period reached ten minutes.

Hemostasis was determined by the cessation of free flow bleeding in less than ten minutes. Gauze pad was used as a negative control.

The hemostatic activity was tested using in vivo porcine spleen biopsy punch model [6 mm wide×3 mm deep], initial tamponade time: 30 s; observation time: 30 s; N=3.

Analysis of the data presented in FIG. 1 indicates that in the porcine spleen biopsy punch model, gelatin with saline and gelatin with galvanic particulates hemostatic materials resulted in average times to hemostasis of over 4.5 minutes. ORC powder based hemostat resulted in average time to hemostasis of over 5 minutes.

Hemostatic material based on gelatin mixed with thrombin, as expected, provided for faster average time to hemostasis of 2.5 minutes. Surprisingly and unexpectedly, the novel hemostatic material of the present invention, based on ORC powder with galvanic particulates, resulted in average time to hemostasis of only 1.5 minutes.

The data presented in FIG. 1 indicates a strong synergistic hemostatic effect of the hemostatic material based on ORC combined with galvanic particulates.

EXAMPLE 3

Galvanic Particulates and ORC Hemostatic Paste Vs. Controls

Figure 2:
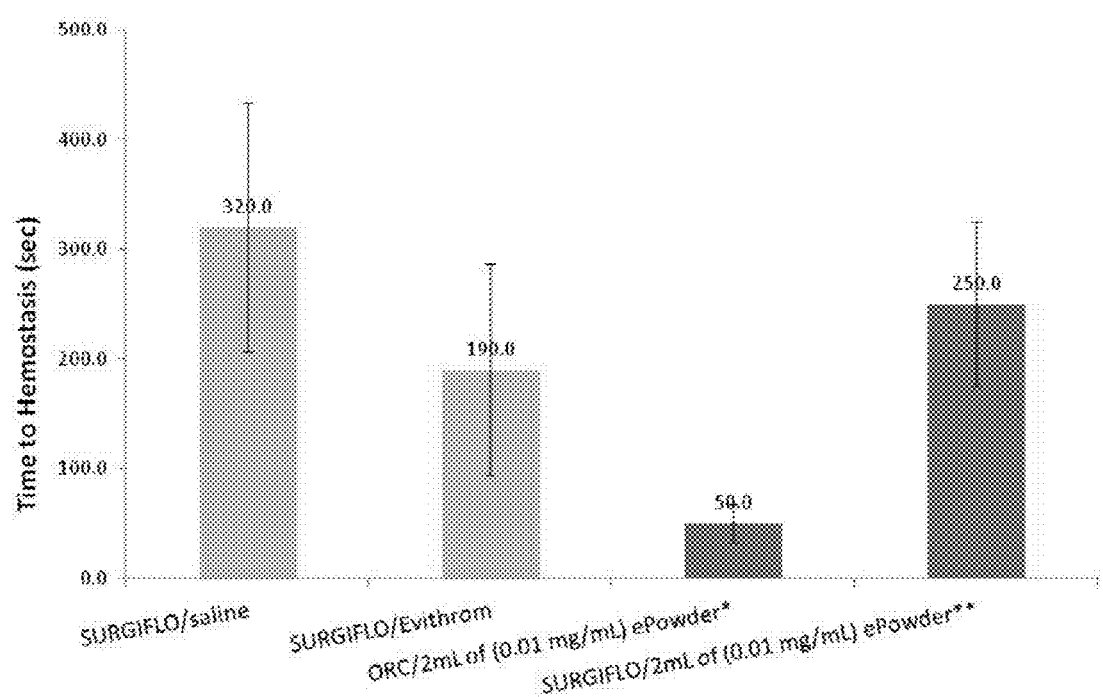
FIG. 2 shows data on time to hemostasis for several tested systems.

Referring now to FIG. 2, data on average time to hemostasis in seconds is presented for several tested systems, including hemostatic material containing ORC, galvanic particulates, and various controls, with typically three experiments conducted with each hemostatic material. The testing articles were prepared similarly to methods described above. The error bars indicate standard deviations. The hemostatic activity was tested using in vivo porcine spleen biopsy punch model as described above, [6 mm wide×3 mm deep], initial tamponade time: 30 s; observation time: 30 s; N=3.

On the chart, designation of SURGIFLO®/saline corresponds to a gelatin based hemostatic material containing SURGIFLO® hemostatic matrix mixed with 2 mL normal saline. On the chart, designation of SURGIFLO®/EVITHROM® corresponds to a gelatin based hemostatic material containing SURGIFLO® hemostatic matrix mixed with 2 mL EVITHROM® thrombin solution (800~1200 IU/mL).

On the chart, designation of ORC/2 mL of (0.001%, 0.01 mg/mL) galvanic particulates corresponds to a hemostatic material containing ORC powder mixed with 2 mL of suspension of galvanic particulates in normal saline containing 0.01 mg/mL of galvanic particles. The resulting concentration of galvanic particulates in the hemostatic material is 0.00067% (0.0067 mg/mL).

On the chart, designation of SURGIFLO®/2 mL of (0.001%, 0.01 mg/mL) galvanic particulates corresponds to a hemostatic material containing SURGIFLO® hemostatic matrix mixed with 2 mL of suspension of galvanic particulates in normal saline containing 0.01 mg/mL galvanic particulates. The resulting concentration of galvanic particulates in the hemostatic material is 0.00025% (0.0025 mg/mL).

Analysis of the data presented in FIG. 2 indicates that the novel hemostatic material of the present invention, based on ORC powder with galvanic particulates, resulted in average time to hemostasis of only 50 seconds. The hemostatic material based on ORC with galvanic particulates exhibited faster time to hemostasis vs. SURGIFLO®; SURGIFLO® with thrombin; and SURGIFLO® with galvanic particulates.

The data presented in FIG. 2 indicate a strong synergistic hemostatic effect of the hemostatic material based on ORC combined with galvanic particulates.

EXAMPLE 4

Varying Concentrations of Galvanic Particulates Plus ORC Hemostatic Paste Vs. Controls Referring now to FIG. 3, data on average time to hemostasis in seconds is presented for two groups of hemostatic materials, specifically hemostatic materials based on gelatin scaffolds (SURGIFLO®-based) and hemostatic materials based on ORC scaffolds, with typically eight experiments conducted with each hemostatic material. The testing articles were prepared similarly to methods described above. The error bars indicate standard deviations. The hemostatic activity was tested using in vivo porcine spleen biopsy punch model as described above, [6 mm wide×3 mm deep], initial tamponade time: 30 s; observation time: 30 s; N=8.

On the chart, the first two bars illustrate control experimental results obtained with gelatin (SURGIFLO®/saline) and with gelatin mixed with thrombin (SURGIFLO®/EVITHROM®). Also presented are data obtained with gelatin scaffold mixed with galvanic particulates, designated as SURGIFLO® based hemostats with five different concentrations of galvanic particulates. The final concentrations of galvanic particulates in matrix ranged from 0.0001% (0.001 mg/mL) to 1% (10 mg/mL).

On the right side of the chart, the experimental data is presented illustrating results obtained with ORC based hemostatic materials, including control comprising ORC/Saline mixture, and ORC powder mixed with galvanic particulates, with five different concentrations of galvanic particulates. The final concentrations of galvanic particulates in matrix ranged from 0.0001% (0.001 mg/mL) to 1% (10 mg/mL).

Figure 3:
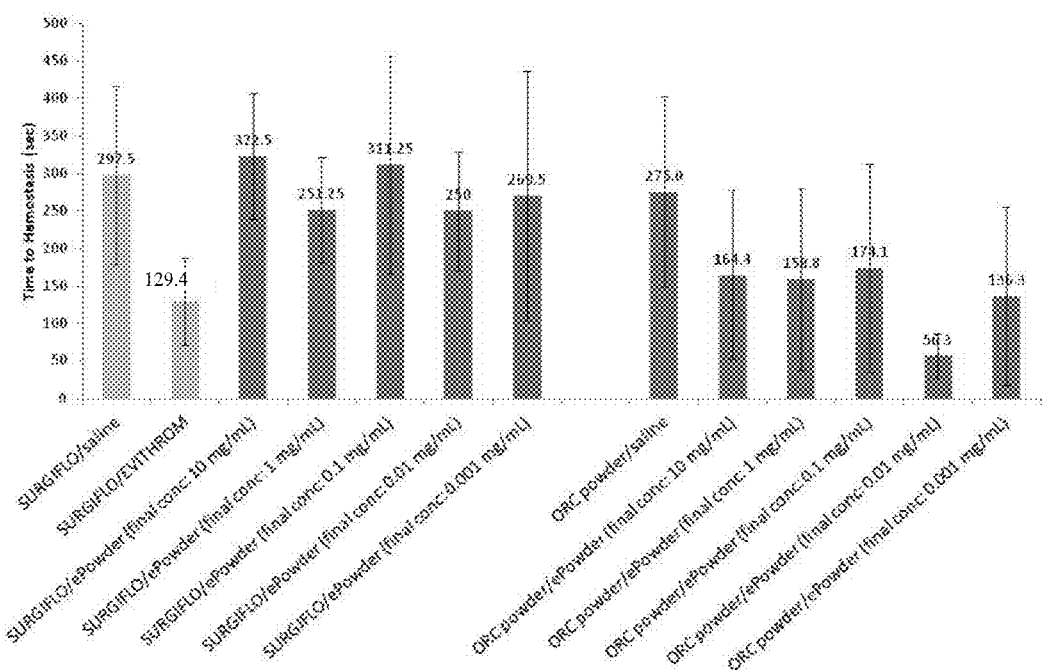
FIG. 3 shows data on time to hemostasis for several tested systems.

Analysis of the data presented in FIG. 3 indicates that all SURGIFLO® based hemostatic materials, with the exception of SURGIFLO® mixed with the thrombin, exhibited average times to hemostasis of 250 seconds or longer. Similarly, ORC powder/saline mixture exhibited average time to hemostasis of 275 seconds.

To the contrary, all hemostatic materials based on ORC powder mixed with galvanic particulates, at all concentrations of galvanic particulates, exhibited shorter average times to hemostasis, ranging from 56 to 174 seconds. These average times to hemostasis are generally comparable to the results obtained with SURGIFLO® mixed with thrombin, and at a final concentration of (0.001%, 0.01 mg/mL) of galvanic particulates in matrix, average time to hemostasis of 56 seconds was more than twice faster vs. average time to hemostasis for thrombin-containing hemostat.

The data presented in FIG. 3 indicate a strong synergistic hemostatic effect of the hemostatic material based on ORC combined with galvanic particulates.

EXAMPLE 5

Galvanic Particles Coated ORC Fabric Vs. Controls

Figure 4:
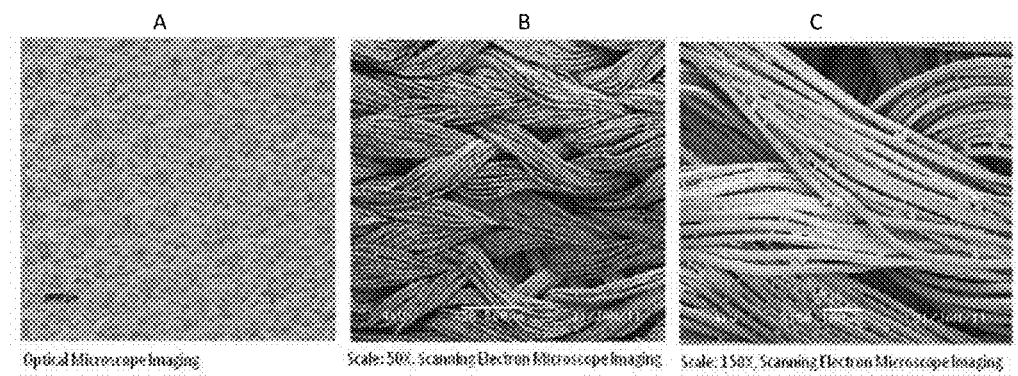
FIG. 4 shows enlarged images of the present invention.

Referring now to FIG. 4, micrographs of galvanic particle coated ORC fabric NU-KNIT are presented, with FIG. 4a representing optical microscope image; FIG. 4b representing SEM image at 50× magnification; and FIG. 4c representing SEM image at 150× magnification. The galvanic particulate is visible on the surface of Nu-knit fabric.

Figure 5:
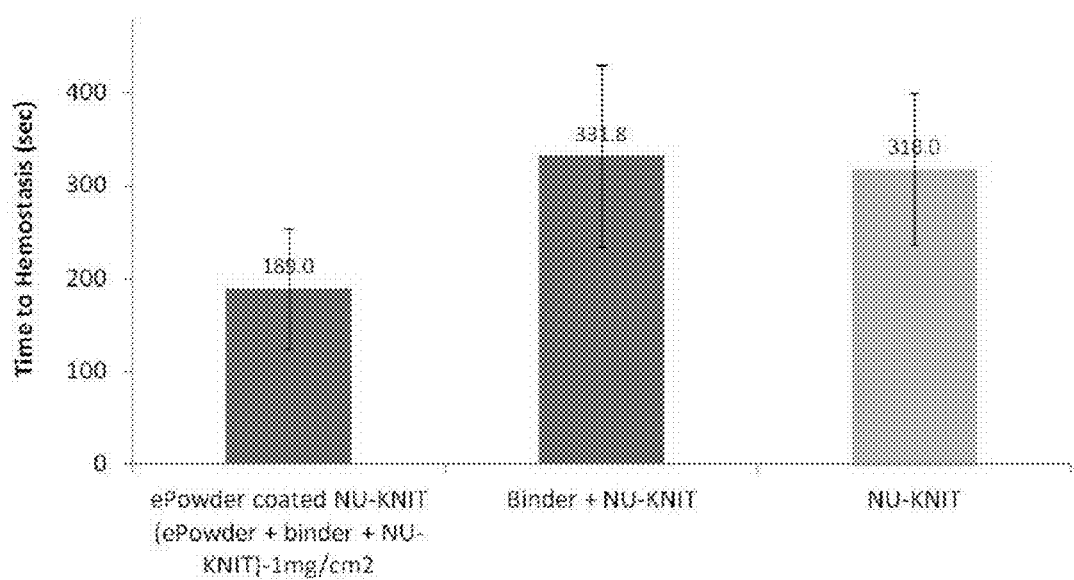
FIG. 5 shows data on time to hemostasis for several tested systems.

Referring now to FIG. 5, data on average time to hemostasis in seconds is presented for Nu-Knit fabric coated with the galvanic particles (1 mg/cm$^2$) with the addition of a binder; Nu-Knit fabric coated with the binder alone, and unadulterated untreated Nu-Knit fabric.

The binder solution was prepared with PEG [mw: 3350 Daltons]/PEG [mw: 8000 Daltons]/dichloromethane (DCM), with a ratio of 1 g:1 g:100 mL (w/w/v). Galvanic particulates were thoroughly mixed with the binder solution in the ratio of 0.1 g/3 mL. The galvanic particulate/binder solution was sprayed onto a pre-trimmed 3"×3" Surgicel Nu-Knit® resorbable hemostat fabric (ETHICON, Inc., Lot #3418584; Exp.: 2014-12). The galvanic particulate coated Surgicel Nu-Knit® was allowed for air dry in a laminar hood for 3 hours following by a vacuum dry for 3 days.

The hemostatic activity was tested using an acute swine spleen incision hemostasis model. In the Linear Incision Spleen Model 15-mm long×3-mm deep incisions were made on the spleen and the test articles were applied to a freshly created wound site followed by an occlusive digital pressure (tamponade). Pressure was initially applied for one minute and was timed using an electronic timer. Following the one-minute initial tamponade, digital pressure was discontinued; the gauze pad on the article was immediately removed. A 30-second hemostasis evaluation period was performed. If free flow bleeding was not observed within 30 seconds, the time to hemostasis was noted, and testing was concluded for that article. If free flow bleeding was observed, pressure and gauze were reapplied for additional 30 second tamponade and observation periods until hemostasis was achieved or until the testing period reached ten minutes. At ten minutes, the trial was aborted as a complete failure and recorded as ">10:00" (greater than ten minutes) in the raw data. Hemostasis was determined by the cessation of free flow bleeding in less than ten minutes.

The data presented in FIG. 5 was collected using in vivo porcine spleen linear incision model as described above; tamponade time: 30 sec; observation time: 30 sec, N=10, with the fabric sample size: 1.5"×1". The error bars indicate standard deviations.

Analysis of the data presented in FIG. 5 indicates that ORC-based Nu-Knit fabric coated with the galvanic particulates with the addition of the binder exhibited much shorter average time to achieve hemostasis vs. Nu-Knit fabric coated with the binder alone, and unadulterated Nu-Knit fabric. The data presented in FIG. 5 indicates a strong synergistic hemostatic effect of the hemostatic material based on ORC combined with galvanic particulates.

EXAMPLE 6

High Concentration Galvanic Particulate Coated ORC Fabric Vs. Controls

Figure 6:
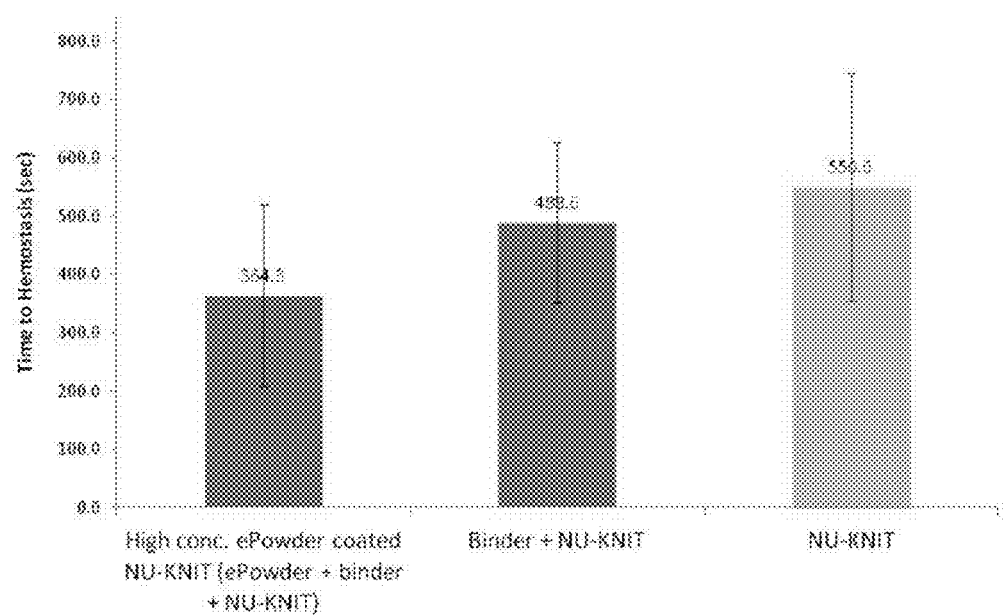
FIG. 6 shows data on time to hemostasis for several tested systems.

Referring now to FIG. 6, data on average time to hemostasis in seconds is presented for Nu-Knit fabric coated with high concentration of galvanic particulates (4.8 mg/cm$^2$) with the addition of the same PEG based binder as explained above; Nu-Knit fabric coated with the binder alone, and unadulterated Nu-Knit fabric. The samples were prepared as described in Example 5 above, with the same concentration of galvanic particulates (0.1 g/3 mL) in the same concentration of the binder mention above. The coating process was repeated for 5 times, separately.

The hemostatic activity was tested using an in vivo porcine partial nephrectomy model, making approximately 2.5±1 cm diameter by 1±0.5 cm depth incisions on kidney and the test articles were applied to a freshly created wound site followed by an occlusive digital pressure (tamponade). Pressure was initially applied for 180 seconds and was timed using an electronic timer. Following the initial tamponade, digital pressure was discontinued; the gauze pad on the article was immediately removed. A 30-second hemostasis evaluation period was performed. If free flow bleeding was not observed within 30 seconds, the time to hemostasis was noted, and testing was concluded for that article. If free flow bleeding was observed, pressure and gauze were reapplied for additional 30 second tamponade and observation periods until hemostasis was achieved or until the testing period reached ten minutes. At 12 minutes, the trial was aborted as a complete failure and recorded as ">12:00" (greater than 12 minutes) in the raw data. Hemostasis was determined by the cessation of free flow bleeding in less than 12 minutes.

The data presented in FIG. 6 was collected using in vivo porcine partial nephrectomy model: 2.5±1 cm deep×1±0.5 cm, Tamponade time: 180 sec; Observation time: 30 sec, N=7; with the hemostatic fabric sample size: 3"×3" and number of tests N=7. The error bars indicate standard deviations.

Analysis of the data presented in FIG. 6 indicates that ORC-based Nu-Knit fabric coated with the higher concentration of galvanic particulates with the addition of the binder exhibited shorter average time to achieve hemostasis vs. Nu-Knit fabric coated with the binder alone, and untreated Nu-Knit fabric. The data presented in FIG. 6 indicates a strong synergistic hemostatic effect of the hemostatic material based on ORC combined with galvanic particulates.

EXAMPLE 7

Figure 7:
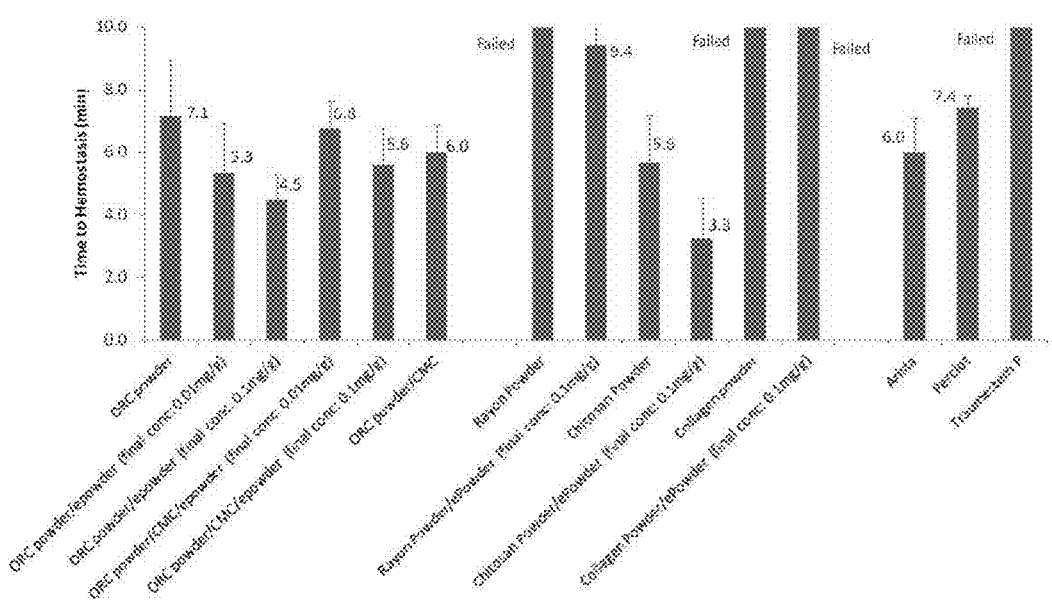
FIG. 7 shows data on time to hemostasis for several tested systems.

Comparisons of Different Scaffold Types in Powder Form With and Without Galvanic Particulates in Animal Model with Compromised Platelet Function Referring now to FIG. 7, data on average time to hemostasis in minutes is presented for several tested systems, all in powder form. The mixtures were formed by thoroughly mixing corresponding powders by placing the powders into a ball mill mixer and milling together for approximately 10-120 minutes depending upon the product millability.

The data presented in FIG. 7 was collected using in vivo porcine spleen biopsy punch model as described above, [6 mm×3 mm]; Initial Tamponade Time: 30 s; Observation Time: 30 s; N=3 or 4. The error bars indicate standard deviations.

The animal model used was hemostatically challenging porcine compromised platelet function model, Female; 4 month-old; 66.1 Kg, with oral medication as follows: 2 days prior to the lab: 300 mg of Plavix and 325 mg of aspirin; 1 day prior to the lab: 75 mg of Plavix and 325 mg of aspirin; the day for the lab: 75 mg of Plavix and 325 mg of aspirin.

The hemostatic powder mixtures were applied to the wound in the amount of 0.2 g pouring the powder onto the bleeding site from a vial.

On the left side of the chart, data for ORC based hemostatic powders are presented, with ORC powder and ORC powder mixture with CMC (carboxymethylcellulose) powder as controls; and ORC powder and ORC+CMC powder mixtures with galvanic particulates at concentrations of 0.01 mg/g and 0.1 mg/g.

CMC powder was made from commercially available Cellulose Gum, sodium carboxymethyl cellulose, 7M8SFPH, Hercules.

In the central area of the chart, the data is presented for scaffolds based on natural hemostatic polymers including Rayon powder, Chitosan powder, and Collagen powder, alone, or in combination with galvanic particulates at concentration of 0.1 mg/g.

Rayon powder was made from rayon fabric.

Chitosan powder used was made from commercially available chitosan, Aldrich, batch #11114TH.

Collagen powder was made from commercially available Instat Pad, collagen absorbable hemostat, ETHICON, Inc., lot #XGP400.

The Rayon, Chitosan, and Collagen powders were made by ball milling in the same way as described above for making ORC powder, but milling for 10~120 min depending upon the material millability.

On the right side of the chart, data for commercially available hemostatic powders are presented, including Arista powder (starch based hemostat) commercially available from Medafor, Minneapolis, Minn., Perclot Powder (starch based hemostat), commercially available from Starch Medical, San Jose, Calif.; and Traumastem Powder (oxidized cellulose based hemostat) commercially available from Bioster A.S., Veverska, Czech Republic.

Analysis of the average times to hemostasis presented in FIG. 7 indicates that in powder form, there was an improved synergistic hemostatic effect for a hemostatic material based on ORC combined with galvanic particulates. In presence of CMC there was no discernable synergistic hemostatic effect of galvanic particulates combined with ORC.

Further analysis of the average times to hemostasis presented in FIG. 7 indicates that in powder form, Rayon powder and collagen powder both exhibited poor hemostatic properties either alone or in combination with galvanic particulates, indicating lack of synergistic hemostatic effect. Notably, charged biopolymer (Chitosan) with incorporated galvanic particulates showed better hemostatic efficacy in presence of galvanic particulates in animal model with compromised platelet function.

Further comparison with other commercially available hemostatic powders indicates that ORC/galvanic particulates mixtures and Chitosan/galvanic particulates mixtures exhibit better hemostatic properties in animal model with compromised platelet function.

EXAMPLE 8

Figure 8:
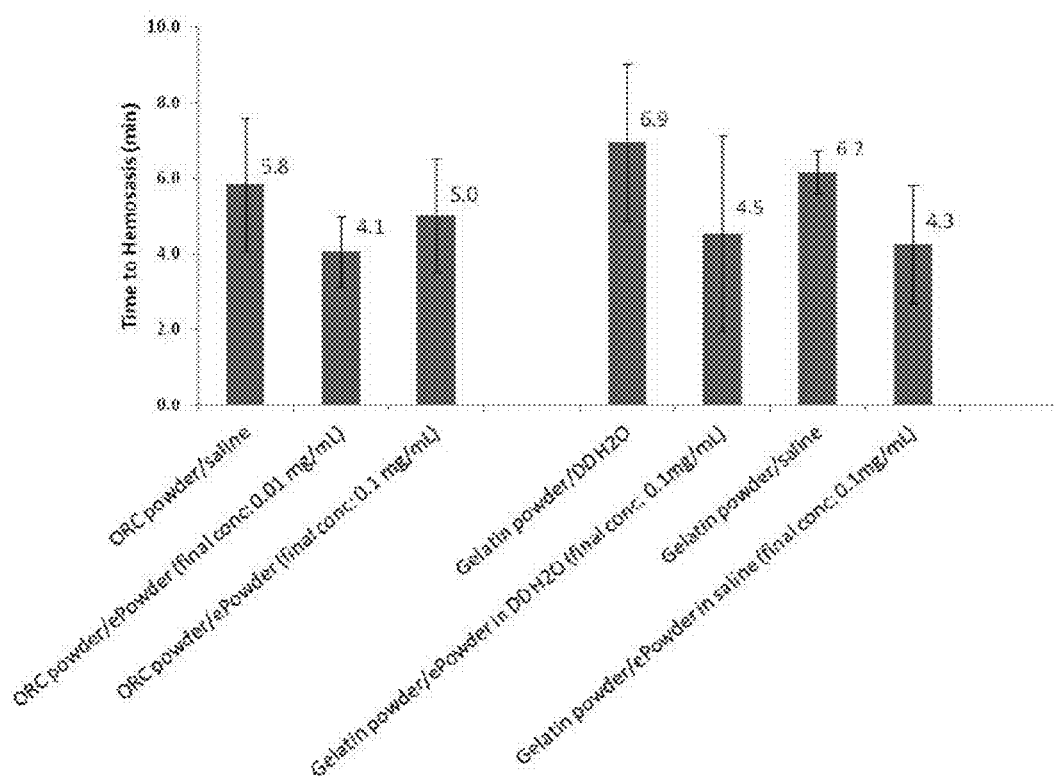
FIG. 8 shows data on time to hemostasis for several tested systems.

Comparisons of Different Scaffold Types in Powder Form With and Without Galvanic Particulates in Animal Model with Compromised Platelet Function Referring now to FIG. 8, data on average time to hemostasis in minutes is presented for several tested systems, all in paste form, for the same hemostatically challenging porcine compromised platelet function model as described in Example 7. The data presented in FIG. 7 was collected using in vivo porcine spleen biopsy punch model as described above, [6 mm×3 mm]; Initial Tamponade Time: 30 s; Observation Time: 30 s; N=3 or 4. The error bars indicate standard deviations.

The ORC powder used was described above. The gelatin powder used was obtained by ball milling Surgifoam® powder, commercially available from Ethicon, Somerville, N.J. The ball milled gelatin had average size of 97 microns. The mixtures were prepared by thoroughly mixing corresponding powders with water or normal saline using mixing syringes as described above.

Analysis of the average times to hemostasis presented in FIG. 8 indicates that in paste form, there was an improved synergistic hemostatic action for a hemostatic material based on ORC combined with galvanic particulates at concentrations of 0.01 mg/mL-0.1 mg/mL.

For the gelatin powder mixed with deionized water (indicated on the chart as DD H2O) or for gelatin mixed with saline, there was a marked acceleration of the hemostatic action upon addition of galvanic particulates at 0.1 mg/mL, indicating a synergistic hemostatic action for the hemostatic material based on gelatin paste with galvanic particulates addition, for either based on purified water or on saline solution. Notably, there was no difference when using saline or pure water, indicating the effect was solution independent.

EXAMPLE 9

Galvanic Particulate Coated ORC Fabric Bactericidal Effect

An additional study was performed by the inventors which demonstrated that galvanic particulate coated ORC showed better zone of inhibition (ZOI) and bactericidal effect compared to ORC alone. ZOI evaluation was performed as follows: Samples were cut in 1 cm$^2$ pieces. Overnight cultures of the challenge bacteria were diluted to get an approximate count of 10$^5$ cfu's/ml. 0.1 ml of this inoculum was placed on the sterile agar plate and spread evenly using the surface spread technique. Samples were slightly hydrated with 0.85% sterile saline prior to transfer on the inoculated agar surface. Care was taken to ensure that the samples were placed flat on the surface and were in complete contact with the inoculum. Plates were incubated at 35 C for 24 hours. After 24 hrs zones were measured from the edge of the sample to the outermost edge of the clear zone. Four measurements around the samples were taken and the average was recorded. After zone measurement the samples were removed and transferred onto a freshly inoculated plate as described above. Daily transfers were made till the sample failed to produce a visible zone around the sample.

Swab test was performed whereby the area under the sample was swabbed to determine if the activity was bactericidal. The swab test was performed as follows: once the zone measurement was recorded and the sample was removed from the plate and transferred to a freshly inoculated plate the clear area under the sample was swabbed using a sterile cotton swab. The swab was transferred onto a sterile plate and the plate was incubated for 24 hours and the results were recorded. The growth from the swab indicated bacteristatic activity and lack of growth indicated bactericidal activity.

Referring now to Table 2, ZOI in mm is shown for the samples of ORC based fabric described in Example 5. Samples were hydrated with 0.85% sterile saline prior to transfer. The results of experiments presented in Table 2 indicate that galvanic particulate-containing ORC fabric exhibited larger ZOI and bactericidal activity against bacterial challenge vs. ORC fabric or ORC fabric with PEG. The activity against gram positive MRSA lasted for up to 2 days and the activity could not be determined for additional days due to breakdown of the sample into a gelatinous mass.

Referring now to Table 3, the results of the Swab test (growth under the lens) are shown. The results of experiments presented in Table 3 indicate that galvanic particulate containing ORC fabric exhibited larger bactericidal effect against bacterial challenges when compared to ORC fabric or ORC fabric with PEG.

Referring now to Table 2, ZOI in mm is shown for the samples of ORC based fabric described in Example 5. Samples were hydrated with 0.85% sterile saline prior to transfer. The results of experiments presented in Table 2 indicate that galvanic particulate-containing ORC fabric exhibited larger ZOI against bacterial challenge vs. ORC fabric or ORC fabric with PEG.

Referring now to Table 3, the results of the Swab test (growth under the lens) are shown. The results of experiments presented in Table 3 indicate that galvanic particulate containing ORC fabric exhibited larger bactericidal effect against bacterial challenges when compared to ORC fabric or ORC fabric with PEG.

TABLE 2

Zone of Inhibition (ZOI)

| SAMPLE ID | Sample description | Bacterial Challenge: Pseudomonas aeruginosa ATCC9027 ZOI, mm | | Bacterial Challenge Meticillin-resistant Staphylococcus aureus MRSA ATCC 33593 ZOI, mm | |
|---|---|---|---|---|---|
| | | Day 1 | Day 2 | Day 1 | Day 2 |
| NK1 | Nu-Knit fabric | 1.8 | 0 | 1.9 | 0 |
| NK2 | Nu-Knit fabric | 1.5 | 0 | 1.6 | 0 |
| EP-NK1 | galvanic particulate coated Nu-Knit fabric | 2.5 | 0 | 2.0 | 1.0* |
| EP-NK2 | galvanic particulate coated Nu-Knit fabric | 2.0 | 0 | 2.0 | 1.0* |
| P-NK1 | PEG-coated Nu-Knit fabric | 1.9 | 0 | 1.6 | 0 |
| P-NK2 | PEG-coated Nu-Knit fabric | 2.2 | 0 | 1.8 | 0 |

*Test stopped due to sample breakdown

TABLE 3

Swab test: growth under the lens

| SAMPLE ID | Sample description | Bacterial Challenge: Pseudomonas aeruginosa ATCC9027 Day 1 | Bacterial Challenge Meticillin-resistant Staphylococcus aureus ATCC 33593 Day 1 |
|---|---|---|---|
| NK1 | Nu-Knit fabric | Growth | no growth/2 cfu |
| NK2 | Nu-Knit fabric | Growth | growth |
| EP-NK1 | galvanic particulate coated Nu-Knit fabric | no growth/ 3 cfu | no growth |
| EP-NK2 | galvanic particulate coated Nu-Knit fabric | no growth | no growth |
| P-NK1 | PEG-coated Nu-Knit fabric | Growth | growth |
| P-NK2 | PEG-coated Nu-Knit fabric | no growth | growth |

EXAMPLE 10

The Effect of Topical Application of Galvanic Particulate Coated ORC for Anti-Inflammatory Activity on Human Epidermal Equivalents was Evaluated as Follows Galvanic particulates used were the same as that described in Example 1.

Epidermal equivalents (EPI 200 HCF), multilayer and differentiated epidermis consisting of normal human epidermal keratinocytes, were obtained from MatTek (Ashland, Mass.). Upon receipt, the epidermal equivalents were incubated for 24 hours at 37° C. in maintenance medium without hydrocortisone. Test materials, including oxidized regenerated cellulose powder (ORC, same as that used in Example 2), CMC powder (7M8SFPH, Hercules.) and galvanic particulates (same of that used in Example 1), were weighed into a container according to Table 4. For Sample No. 1-13, 4 ml of normal saline was added to each powder mixture and 4 ml of de-ionized water for Sample No. 14. Each sample was then mixed by a vortex mixer vigorously to form a uniform suspension. The numbers in the parenthesis in Table 4 represent the final weight percentage of each test material.

TABLE 4

In Vitro Anti-inflammatory Test using Epidermal Equivalents (EPI 200 HCF) Model

| Test Group | Test Materials | ORC (Wt %) | CMC (Wt %) | Galvanic Particulate (Wt %) |
|---|---|---|---|---|
| 1 | ORC alone | 1 g (20%) | 0 | 0 |
| 2 | CMC alone | 0 | 50 mg (1%) | 0 |
| 3 | ORC/CMC | 1 g (20%) | 50 mg (1%) | 0 |
| 4 | ORC/CMC/ Galvanic Particulate | 1 g (20%) | 50 mg (1%) | 0.01 mg (0.0002%) |
| 5 | ORC/CMC/ Galvanic Particulate | 1 g (20%) | 50 mg (1%) | 0.1 mg (0.002%) |
| 6 | ORC/CMC/ Galvanic Particulate | 1 g (20%) | 50 mg (1%) | 1 mg (0.02%) |
| 7 | ORC/CMC/ Galvanic Particulate | 1 g (20%) | 50 mg (1%) | 5 mg (0.1%) |
| 8 | ORC/CMC/ Galvanic Particulate | 1 g (20%) | 50 mg (1%) | 10 mg (0.2%) |
| 9 | ORC/ Galvanic Particulate | 1 g (20%) | 0 | 0.01 mg (0.0002%) |

TABLE 4-continued

In Vitro Anti-inflammatory Test using Epidermal Equivalents (EPI 200 HCF) Model

| Test Group | Test Materials | ORC (Wt %) | CMC (Wt %) | Galvanic Particulate (Wt %) |
|---|---|---|---|---|
| 10 | ORC/ Galvanic Particulate | 1 g (20%) | 0 | 0.1 mg (0.002%) |
| 11 | ORC/e Galvanic Particulate | 1 g (20%) | 0 | 1 mg (0.01%) |
| 12 | ORC/ Galvanic Particulate | 1 g (20%) | 0 | 5 mg (0.02%) |
| 13 | ORC/ Galvanic Particulate | 1 g (20%) | 0 | 10 mg (0.1%) |
| 14 | Galvanic Particulate | 0 | 0 | 40 mg (1%) |

Exactly six (6) micro liters of each suspension was applied to each well of Mitek Epidermal equivalents two (2) hours before exposure to solar ultraviolet light (1000W-Oriel solar simulator equipped with a 1-mm Schott WG 320 filter; UV dose applied: 70 kJ/m$^2$ as measured at 360 nm) to induce inflammation response. The samples were run in triplicates. The equivalents were incubated for 24 hours at 37° C. with a maintenance medium, and then the supernatants were analyzed twice for IL-1alpha cytokine release using commercially available kits (Upstate Biotechnology, Charlottesville, Va.). The test results are shown in Table 5.

TABLE 5

Result of anti-inflammatory test for IL-1alpha cytokine reduction in comparison to ORC alone as control using Epidermal equivalents (EPI 200 HCF) model

| Test Group | Test Materials | Mean IL-1alpha (pg/ml) | Standard Deviation IL-1alpha (pg/ml) | Percentage Inhibition of Skin Inflammation (compared to ORC alone) |
|---|---|---|---|---|
| 1 | ORC (20%) alone | 497 | 135 | 0 |
| 2 | CMC(1%) alone | 446 | 96 | 10 |
| 3 | ORC (20%)/CMC (1%) | 421 | 115 | 15 |
| 4 | ORC (20%)/CMC (1%)/ Galvanic Particulate (0.0002%) | 375 | 60 | 25 |
| 5 | ORC (20%)/CMC (1%)/ Galvanic Particulate (0.002%) | 428 | 132 | 14 |
| 6 | ORC (20%)/CMC (1%)/ Galvanic Particulate (0.02%) | 255 | 77.4 | 49 |
| 7 | ORC (20%)/CMC (1%)/ Galvanic Particulate (0.1%) | 238 | 56.8 | 48 |
| 8 | ORC (20%)/CMC (1%)/ Galvanic Particulate (0.2%) | 254 | 135 | 49 |
| 9 | ORC (20%)/Galvanic Particulate (0.0002%) | 366 | 124 | 26 |
| 10 | ORC (20%)/Galvanic Particulate (0.002%) | 464 | 166 | 7 |
| 11 | ORC (20%)/Galvanic Particulate (0.02%) | 302 | 88.1 | 39 |
| 12 | ORC (20%)/Galvanic Particulate (0.1%) | 176 | 67.7 | 65 |
| 13 | ORC (20%)/Galvanic Particulate (0.2%) | 142 | 108 | 71 |
| 14 | Galvanic Particulate (1%) | 218 | 90.6 | — |

It can be seen from Table 5 that combinations of ORC powder with galvanic particulate resulted in reduction of inflammatory cytokine IL-1alpha. It is well known that excess inflammation is associated with healing impairment (Inflammation in wound repair: molecular and cellular mechanisms, S. A. Eming, et. al., Journal of Investigative Dermatology, 2007, Vol. 127, p 514-525). It has also been reported a special form of electrical stimulation inhibited inflammation and enhanced healing in human subjects (Acceleration of cutaneous healing by electrical stimulation: Degenerate electrical waveform down-regulates inflammation, up-regulates angiogenesis and advances remodeling in temporal punch biopsies in a human volunteer study, A. Sebastian, et. al., Wound Repair and Regeneration, 2011, Vol. 19, p 693-708). The results of this test indicate the combination of ORC powder with galvanic particulate may provide the benefit of healing enhancement in addition to improved hemostatic efficacy.

EXAMPLE 11

ORC and Galvanic Particulates Vs. Controls In Vitro Clotting Study

In a bench top experiment, ORC powder alone and ORC powder combined with galvanic particulates were tested to evaluate interaction with heparinized porcine blood. Nine thousand (9000) IU of heparin solution was initially applied to a 45.9 kg female porcine. The activated clotting time (ACT) was maintained above 300 seconds by infusing an additional 2000 IU heparin solution where needed.

The blood was stored in BD Vacutainer® tubes with 3.2% sodium citrate with a ratio of 4.5 mL of blood to 0.5 mL of 3.2% sodium citrate. The blood was then diluted with normal saline solution with a ratio of 1 to 1 (v/v) prior to testing. Clotting samples were prepared by adding 1 mg of ORC powder or 1 mg of ORC plus galvanic particulates (with a mixing ratio of g ORC combined with 0.1 mg galvanic particulate) onto each 20 μL droplet of blood on the surface of a glass slide. A brownish gelatinous mass indicating clotting was observed for ORC powder plus galvanic particulates within a few seconds, while for ORC powder alone much slower clotting of less brownish color was observed, even after about 2 minutes. This indicated that ORC powder/galvanic particulates promoted more rapid blood coagulation than ORC alone.

Similar observations were obtained using normal non-heparinized porcine blood in another bench top experiment. The blood was stored in BD Vacutainer® tubes with 3.2% sodium citrate with a ratio of 4.5 mL of blood to 0.5 mL of 3.2% sodium citrate.

The blood was diluted with normal saline with a ratio of 1 to 1 in volume prior to use. ORC powder, ORC powder/galvanic particulates with a ratio of 1 g ORC/0.1 mg galvanic particulates, galvanic particulates, and control solution of normal saline were tested to evaluate interaction with blood and clotting. Samples were prepared by adding 100 mg of ORC, 100 mg ORC+ galvanic particulates, or 0.01 mg of galvanic particulates described above, to separate glass vials containing 2 mL of diluted porcine blood. Each vial containing blood and sample was gently turned up-side-down three times, and placed on the table for 90 seconds. Clotting of blood in each vial was observed after 90 seconds. No clotting was observed in the vial with the control solution of normal saline and galvanic particulates. A more complete clotting of blood was observed in the vial containing ORC plus galvanic particulates, while less complete clotting of blood was observed in the vial with ORC alone.

While the above examples demonstrate certain embodiments of the invention, they are not to be interpreted as limiting the scope of the invention, but rather as contributing to a complete description of the invention.

We claim:

1. A hemostatic material, comprising a) at least one galvanic particulate comprising of at least two dissimilar metals, and b) a polysaccharide-based, biocompatible hemostatic scaffold, wherein said scaffold is oxidized regenerated cellulose in powder form.

2. The hemostatic material of claim 1, wherein said galvanic particulate comprises copper and zinc.

3. The hemostatic material of claim 1, comprising 0.01-10 mg of galvanic particulate per gram of the scaffold.

4. The hemostatic material of claim 1, wherein said hemostatic material further comprises a binder.

5. The hemostatic material of claim 4, wherein said hinder is polyethylene glycol.

6. The hemostatic material of claim 5, comprising 0.01-10 mg of galvanic particulate per sq. cm of the scaffold.

7. A method of providing a hemostatic treatment to a wound site, comprising the steps of:
   (a) forming a hemostatic material comprising a scaffold in the form of oxidized regenerated cellulose in powder form, a galvanic particulate comprising at least two dissimilar metals and optionally a mixing medium;
   (b) immediately applying the hemostatic material to tile wound site.

8. A method of making a hemostatic material comprising the steps of:
   (a) providing at least one galvanic particulate comprising particles made of at least two dissimilar metals and a hemostatic scaffold;
   (b) distributing said galvanic particulate in said scaffold or on the surface of said scaffold, wherein the scaffold is composed of oxidized regenerated cellulose in powder form.

9. The method of claim 8, wherein a plurality of galvanic particulates are distributed substantially homogenously throughout the scaffold.

10. The method of claim 8, wherein a plurality of galvanic particulates are provided on at least one major surface of the scaffold.

11. The method of claim 8, further comprising the step of providing water and mixing said water with oxidized regenerated cellulose (ORC) and the at least one galvanic particulate.

12. The method of claim 7 wherein the hemostatic treatment material is used on a patient having platelet compromised blood or heparinized blood or otherwise containing anti-clotting or anti-coagulant agents.

* * * * *